United States Patent [19]

Rotman

[11] Patent Number: 4,937,187

[45] Date of Patent: Jun. 26, 1990

[54] METHODS FOR SEPARATING MALIGNANT CELLS FROM CLINICAL SPECIMENS

[75] Inventor: M. Boris Rotman, Jamestown, R.I.

[73] Assignee: Brown University Research Foundation, Providence, R.I.

[21] Appl. No.: 11,219

[22] Filed: Feb. 5, 1987

Related U.S. Application Data

[63] Continuation-in-part of Ser. No. 623,183, Jun. 22, 1984, Pat. No. 4,734,372, which is a continuation-in-part of Ser. No. 463,669, Feb. 4, 1983, Pat. No. 4,559,299.

[51] Int. Cl.$^5$ ............................................. C12O 1/24
[52] U.S. Cl. ...................................... 435/30; 435/34; 435/240.21; 435/267; 435/268; 435/803; 435/261; 436/63; 436/800; 436/813
[58] Field of Search ................... 435/30, 34, 240.21, 435/262, 267, 268, 803, 261; 436/63, 800, 813

[56] References Cited

U.S. PATENT DOCUMENTS

| | | | |
|---|---|---|---|
| 3,073,746 | 1/1963 | Thompson et al. | 435/240.21 X |
| 3,586,859 | 6/1971 | Katz et al. | 250/83.3 |
| 3,821,087 | 6/1974 | Knazek et al. | 195/127 |
| 3,853,712 | 12/1974 | House et al. | 195/127 |
| 3,948,732 | 4/1976 | Haddad et al. | 195/127 |
| 4,184,922 | 1/1980 | Knazek et al. | 435/284 |
| 4,201,845 | 5/1980 | Feder et al. | 435/285 |
| 4,220,725 | 7/1980 | Knazek et al. | 435/285 |
| 4,241,187 | 12/1980 | White | 435/284 |
| 4,242,459 | 12/1980 | Chick et al. | 435/283 |
| 4,308,351 | 12/1981 | Leighton et al. | 435/284 |
| 4,332,893 | 6/1982 | Rosenberg | 435/240.21 X |
| 4,350,768 | 9/1982 | Tihon et al. | 435/803 X |
| 4,391,912 | 7/1983 | Yoshida et al. | 435/241 |
| 4,423,145 | 12/1983 | Stampfer et al. | 435/240.23 X |
| 4,537,860 | 8/1985 | Tolbert et al. | 435/240 |
| 4,554,251 | 11/1985 | Hink, Jr. | 435/240.21 |
| 4,559,299 | 12/1985 | Rotman | 435/29 |
| 4,582,787 | 4/1985 | Frankel | 435/5 |

FOREIGN PATENT DOCUMENTS

8403047 8/1984 World Int. Prop. O.

OTHER PUBLICATIONS

Rotman, Boris & Papermaster, Ben W., "Membrane Properties of Living Mammalian Cells as Studied by Enzymatic Hydrolysis of Fluorogenic Esters", *Proceedings of the National Academy of Sciences*, vol. 55, No. 1, pp. 134-141, Jan. 1966.

Knazek, Richard A., *Fed. Pro.*, vol. 33, No. 8, 1974, pp. 1978-1981, "Solid Tissue Masses Formed in Vitro From Cells Cultured on Artificial Capillaries".

Salmon, Sydney E. et al., *The New England Journal of Medicine*, vol. 298, pp. 1321-1327, (Jun. 15, 1978), "Quantitation of Differential Sensivity of Human-Tumor Stem Cells to Anticancer Drugs".

Buick et al., *Cancer Research*, vol. 39, pp. 5051-5056 (1979), "Development of an Agar-Methyl Cellulose Clonogenic Assay for Cells in Transitional Cell Carcinoma of the Human Bladder".

Von Hoff et al., *Cancer*, vol. 50, pp. 696-701 (1982), "Direct Cloning of Human Malignant Melanoma in Soft Agar Culture".

Tsuda et al., "Investigation of Factors Involved in the uptake Velocity of Flourescein Diacetate and Intracellular Flouresience Polarization Valve, I. Physiological Aspects in Lymphoblastoid Cells", *Cell Structure and Function*, vol. 7, pp. 166-175 (1982).

Maeda et al., "Investigation of Factors Involved in the uptake Velocity of Fluorescein Diacetate and Intracellular Fluorescecen Polarization Value II, Cytotoxicity Produced by Anticancer Agents", *Cell Structure and Function*, vol. 7, pp. 177-182 (1982).

Rotman, "Assessment of Drug Sensitivity in Organ Cultures from Individual Human Biopsies", Proceeding of the *American Association for Cancer Research* (1985).

*Primary Examiner*—Sam Rosen
*Attorney, Agent, or Firm*—Thomas J. Engellenner

[57] ABSTRACT

Fragments of a biopsy sample on the order of about 50 to 5000 cells are preferred for establishing viable tumor cell cultures for purposes such as establishing cell lines, chemotherapeutic assays and the like. Such fragments retain the three-dimensional cellular structure or organization of the original tumor and, therefore, can be cultured more readily. To obtain such fragments suitable for culturing, the biopsy sample can be enzymatically digested in a proteolytic or nucleolytic enzyme, such as collagenase, or by mechanical dissociation, or both where necessary. The fragments can then be suspended in an aqueous medium so that non-aggregated cells (e.g., red blood cells, lymphocytes, macrophages) and cellular debris will form a supernatant while the remaining fragments containing aggregated tumor cells are deposited in a sediment layer. Preferably, the medium is an isotonic tissue culture medium and decantation is conducted at least twice; first in a serum-containing medium and then, secondly, in a serum-free medium. Fragments containing living tumor cells can be selected by fluorochromasia, that is, by contacting the sedimented layer with a fluorogenic substrate such that viable tumor cells take up and hydrolyse the substrate, and then exhibit fluorescence. Cytotoxicity assay protocols employing tumor cell aggregates prepared by the present techniques are also disclosed.

19 Claims, No Drawings

METHODS FOR SEPARATING MALIGNANT CELLS FROM CLINICAL SPECIMENS

REFERENCE TO RELATED APPLICATIONS

This application is a continuation-in-part of the U.S. patent application Ser. No. 623,183 filed June 22, 1984 now U.S. Pat. No. 4,739,372, entitled "Cell Culturing Methods And Apparatus," which is a continuation-in-part of U.S. patent application Ser. No. 463,669 filed Feb. 4, 1983, now U.S. Pat. No. 4,559,299, entitled "Cytotoxicity Assays In Cell Culturing Devices," the disclosures of which are hereby incorporated by reference.

BACKGROUND OF THE INVENTION

The technical field of this invention is cell culturing and, in particular, methods for separating malignant cells from biopsy samples or other clinical specimens.

The culturing of cancerous or otherwise abnormal cells has become an important tool of clinicians and researchers combating the diseases which such cells manifest. Because cancerous cells of identical histopathological type show a wide range of responsiveness to particular drug therapies among individual patients, predictive techniques, similar to the culture and sensitivity assays used for the management of microbial infections, have become valuable techniques for selecting effective chemotherapy in individual cases. Quick and effective culturing techniques are essential to such predictive assays.

Similarly, the culturing of cells from biopsy samples has also become important in establishing cell lines. Tumor registries provide standardized tumor cell lines, against which new drugs and other agents can be tested to screen for more effective modalities of treatment. Thus, effective techniques for separating malignant cells from clinical specimens are also essential to the establishment of primary cultures which can be expanded into cell lines for screening purposes.

Early predictive assay techniques involved the cloning of single cell suspensions from biopsy specimens in soft agar after brief exposure to particular anti-cancer drugs. These agar culture techniques often suffered from low plating efficiency and poor correlation with actual treatment results. See Salmon et al., "Quantitation Of Differential Sensitivity Of Human Stem Cells To Anti-Cancer Drugs," Vol. 298 *New England Journal of Medicine*, pp. 1321-1327 (1978); Buick et al., "Development Of An Agar-Methyl Cellulose Clonogenic Assay For Cells In Transition Cell Carcinoma Of The Human Bladder," Vol. 39 *Cancer Research*, pp. 5051-5056 (1979) and Von Hoff et al., "Direct Cloning Of Human Malignant Melanoma In Soft Agar Culture," Vol. 50 *Cancer*, pp. 695-701 (1982), for further details on agar culture techniques.

Another predictive system which has been proposed for chemotherapy studies involves the growth of cancer cells in vessels fed by a matrix of synthetic, hollow fiber capillaries. In such systems, single cell suspensions from biopsy samples were again used to seed the artificial capillary vessel. See, for example, Quartles et al., "Hemodialysis-Matrix Profusion Culture System: A New Technique For Studying Chemotherapeutic Activity In Tumor Cells," Vol. 16 *In Vitro*, p. 246 (1980). For a review of capillary cultures, generally, see Schratter, "Cell Culture With Synthetic Capillaries," Vol. XIV *Methods In Cell Biology*, pp. 95-103 (1976).

In U.S. Pat. No. 4,559,290, the present applicant has disclosed a simple, sensitive assay technique in which cancerous or otherwise abnormal cells can be cultured and their response to chemotherapeutic agents evaluated by measuring the retention of fluorescein or similar label by living cell membranes. The cultured cells are allowed to accumulate fluorescein by contact with a fluorogenic substrate, typically a nonpolar ester of fluorescein and an aliphatic acid, introduced into the cell culture. The fluorogenic substrate penetrates the cell membranes where it is enzymatically hydrolyzed, liberating fluorescein and staining the cell brightly fluorescent under blue light. Since fluorescein, a negatively charged molecule, does not diffuse readily across the cytoplasmic membrane of normal cells, the process causes intracellular accumulation of fluorescein in living cells. However, when a dead cell is treated with a fluorogenic substrate, no intracellular accumulation of fluorescein is observed.

One of the problems which has plagued clinicians and researchers in conducting chemotherapeutic assays and the like is the need to separate from a biopsy sample those cells which are responsible for the malignancy and then to culture such cells in a manner that mimics in vivo conditions. The conventional techniques for preparing cell lines involve the complete dissociation of the tumor specimens into single cell suspensions Unfortunately, such suspensions often contain a large number of normal cell which are very difficult to separate from tumor cells.

Moreover, when single cell suspensions are used for assay purposes, or even when cell lines are grown from such single cells, tests conducted on such cultures often are poorly correlated with actual results in patient treatment. The destruction of the primary tissue architecture has been shown to affect not only cellular ability to survive under culture conditions but drug sensitivity to anticancer agents as well. See, generally, Miller, B. E. et al. "Interactions between tumor subpopulations affecting their sensitivity to the antineoplastic agents cyclophosphamide and methotrexate." Vol. 41 *Cancer Res.*, pp. 4378-4381 (1981) and Rasey, J. S. and Nelson, N. J. "Response of an in vivo-in vitro tumor to X-rays and cytotoxic drugs: effect of tumor disaggregation method on cell survival." Vol. 41, *Br. J. Cancer Suppl. IV*: pp. 217-221 (1980).

Thus, there exists a need for better techniques for preparing biopsy samples for use in predictive assays. A simple, effective way of separating viable malignant cells, substantially free of extraneous (i.e., non-malignant) cells would satisfy a long-felt need in the field.

SUMMARY OF THE INVENTION

It has been discovered that the complete dissociation of a tumor specimen into a single cell suspension is not necessary for the purposes of separating malignant from non-malignant cells, and it is instead preferable to employ fragments of the specimen (i.e., fragments on the order of 50-5000 cells) for assay purposes. Techniques are disclosed herein for substantially liberating such fragments from the normal cells, interstitial material and cellular debris that typically make up a biopsy sample. Additionally, the fragments obtained by the methods of the present invention retain the three-dimensional structure or organization of the original tumor and, therefore, can be cultured much more readily.

In another aspect of the invention, fluorochromasia is used to distinguish fragments containing living tumor cells from otherwise similar-appearing aggregates of dead cells. Viable tumor cell-containing fragments will take up a fluorogenic substrate and can be selected by their fluorescence. When this selection technique is used in conjunction with the preparatory steps, the efficiency of converting biopsy samples into preparations containing mainly viable tumor cells is greatly enhanced.

A typical protocol according to the invention calls for partial dissociation of the biopsy sample by enzymatic or mechanical means, or a combination of such treatments, to obtain fragments on the order of about 50 to 5000 cells. Preferably, the specimen is mechanically cleaved or diced and then subjected to further mechanical dissection by a shearing device. Alternatively or additionally, the specimen can be treated with proteolytic and/or nucleolytic enzymes. Preferred proteolytic enzymes include collagenase, trypsin and chymotrypsin. Most preferably, the enzyme is collagenase, particularly when the tumor type is one which contains collagen (e.g., a breast tumor). Additionally, nucleolytic enzymes, such as DNAases and RNAases, can be used to lyze dead cells and, thereby, further aid in the fragmentation of the specimen.

The resulting fragments are then suspended in an aqueous medium such that non-aggregated cells (e.g., red blood cells, lymphocytes, macrophages) and cellular debris will form a supernatant while the aggregates of tumor cells are deposited in a sediment layer. The aqueous medium is preferably an isotonic tissue culture medium and decantation preferably is conducted at least twice; first, in a serum-containing medium and then, secondly, in a serum-free medium.

The resulting sediment can be placed in a Petri dish or the like and fluorogenic substrate added. After a short period of time, the clumps which take up the substrate can be visualized by their fluorescence and then can be removed with a pippette.

This technique is far less cumbersome than prior art techniques for separating tumor cells from normal cells by specific gravity in a centrifuge (e.g., against an albumin gradient). Moreover, the viability of tumor cell lines obtained by the techniques of the present invention appears to be considerably better than that obtained by conventional techniques.

The invention will next be described in connection with certain preferred embodiments. However, it should be clear that those skilled in the art can make various modifications, additions and subtractions to the techniques disclosed herein without departing from the spirit or scope of the invention. For example, it should be clear that the steps disclosed herein can be performed manually or by automated processes or by a combination of manual and automated steps. Optimal protocols for mechanical and/or enzymatic dissociation, including the preferred concentrations of enzyme reagents and the duration of such chemical treatments will depend upon the particular tumor type treated and can be determined by the practitioner without undue experimentation.

DETAILED DESCRIPTION

Human solid tumor biopsies can be placed in a cold tissue culture medium such as RPMI 1640 supplemented with 10 percent fetal bovine serum, penicillin-streptomycin (100 units/ml) and gentamycin (50 ug/ml) for transportation to the laboratory. The biopsy tissue can be fragmented, for example, by first mincing it with scalpels to obtain pieces of about 0.3 to about 5.0 cubic millimeters, preferably about 1.0 cubic millimeters, and then subjecting the minced pieces to shearing forces (while suspended in culture medium) using an automated shearing machine (available commercially from a variety of sources, such as Tekmar, Inc., Cincinnati, Ohio) for a brief period of time (e.g., 2–5 seconds).

Biopsy samples showing poor cellularity, such as typically found in breast tumor samples, can be treated enzymatically to degrade the collagen present in the sample. Such specimens can be minced as described above and then suspended in collaganase. In one preferred procedure, the tumor samples are minced and then suspended in the above-described medium, supplemented with about 0.2 mg/ml of collagenase and incubated overnight at about 37° C. on a rocking platform (e.g., at about 2 strokes per minute) under 5% $CO_2$. The suspension can be further subjected to shearing, as described above, if necessary to obtain cellular fragments of the appropriate size. The order of mechanical and enzymatic treatments can also be reversed and, in some instances, enzymatic digestion alone can be practiced to obtain appropriately sized fragments.

Preferably, the fragments obtained by the above-described procedures will contain from about 50 to about 5000 cells. The fragments are suspended in the above described medium or an equivalent isotonic aqueous medium and allowed to stand for about 5 minutes. During this time, non-aggregated cells (e.g., red blood cells, lymphocytes, macrophages) interstitial materials and cellular debris will form a supernatant while the aggregates of tumor cells are deposited in a sediment layer. The medium and supernatant can be decanted and discarded. Preferably, decantation is conducted at least twice, first in a serum-containing medium and then in a serum-free medium.

The resulting sediment can then be placed in a Petri dish or the like for fluorochromatic selection of viable tumor cell aggregates. In the Petri dish, the tumor cell aggregates can be incubated in the presence of a fluorogenic substrate, such as fluoroscein mono- or di-acetate and viable cell aggregates can be by fluorochromasia, that is, by their characteristic rapid accumulation of intercellular fluorescein. Flurochromasia is the result of enzymatic hydrolysis of lipophilic fluorogenic substrates, such as fluorescein esters of fatty acids. In contrast, dead cells do not show cytoplasmic retention of fluorescein. Hence, aggregates of viable tumor cells suitable for culturing can be selected by manual or automated means based upon exhibition of fluorochromasia. Such cell aggregates can be used to establish cell lines for drug screening purposes or as seed cultures for cytotoxicity assays.

The method described above separates tumor fragments by minimally disruptive procedures that preserve the in vivo patterns characteristic of malignant growth. Morphological criteria indicate that this method yields cell aggregates consisting exclusively of viable tumor cells. Samples from malignant tumors of various histological types and primary anatomic sites were examined histologically. The samples consisted of viable cell aggregates prepared according to the invention and randomly selected by their fluorochromasia. From 34 different tumors, 270 aggregates ranging from about $0.1 \times 0.1$ mm to about $0.3 \times 0.5$ mm in size, containing from about 100 to 1600 cells each, were examined. None of the samples were found to contain normal stromal cells. In addition, comparative electron microscopic studies on both pre and post cultured aggregates (1-27 days after culture) on 10 tumors showed excellent ultrastructural cellular preservation with striking retention of tumor organellar differention.

The techniques described above are particularly well suited for selecting tumor cell aggregates for use in predictive chemotherapeutic assays. In one exemplary protocol, biopsy samples of breast adenocarcinomas were obtained and fragmented as described above. The viable tumor aggregates were collected and then divided into 8 to 10 cultures, of which two were left untreated as controls. The remaining cultures were used in duplicate for drug testing. The culture chambers were constructed in accordance with the teachings of the above-referenced U.S. Ser. No. 623,183. Specifically, matrices of woven paper membrane material (e.g., "teabag" paper from C. H. Dexter, Windsor Locks, Conn.) supported by a grid of 20 mesh stainless steel screen were fitted into wells of Limbro plates (Falcon No. 3047, Becton Dickinson Co., Oxnard, Calif.).

Shortly before planting the tumor aggregates, a small volume (about 30 microliters) of a collagen solution (obtained by diluting a 3 mg/ml purified collagen solution (Collagen Corp., Palo Alto, Calif.) with a concentrated solution of Dulbecco's modified eagle powder medium, fetal bovine serum and the above described culture medium in the proportion 3.0:0.5:0.25:1.0, respectively) was coated onto the stainless steel grids in the wells of the Limbro plate. The plate was kept in a 95% air-5% $CO_2$ atmosphere (to keep neutral pH) until ready for use. Several pieces of teabag paper (previously folded, placed in saline and autoclaved) were layed on top of sterile filter paper (Whatman 3 MM). Tumor fragments were then deposited on the folded part (double layer) of each piece of teabag paper, and the hanging part of the paper (single layer) was folded over the cells thus creating a "sandwich." The plate containing the collagen-treated grids was taken out of the incubator, and each of the "sandwiches" were deposited on a grid. The plate was incubated at 37° C. overnight under 95% air-5% $CO_2$.

The cultures of tumor cell aggregates in the individual wells were maintained in the above-described supplemented RPMI 1640 culture medium for the duration of the assay period, except when fluorochromatic measurements were taken. Various drugs (e.g., doxorubicin) and various dosages were administered to the cell cultures in each well. Two or more of wells were left untreated to control for cellular growth and viability during the culture time period. A base line measurement of each well was taken on Day 2. To measure culture viability in situ, the medium was removed from the cultures and a fluoroscein monoacetate solution was added (prepared from a stock fluoroscein monoacetate in acetone solution (5 mg/ml) diluted with serum-free (25 mM HEPES) RPMI medium).

After a thirty-minute incubation at room temperature, the fluorogenic substrate was replaced with regular growth medium and the plate was left at room temperature for about 5 minutes. The medium was again replaced and the cultures were examined under blue light (100-W tungsten lamp with a BH-12 (Zeiss, Germany) broad band blue filter. Fluorescence microphotographic records were obtained under low power (7x) using an Olympus stereo microscope filled with a filter (Kodak-Wratten No. 15 barrier filter) to exclude blue light. Photographic exposures were 6 to 10 seconds using Kodak Tri-X film.

On Day 3, drugs at indicated concentrations were added to the cultures. On Day 4, the culture medium was replaced with fresh medium. On Day 7, and at appropriate intervals thereafter, photographic records of in situ cellular viability were obtained as before. All drugs were used at concentrations comparable to those in plasma as indicated by pharmacokinetic data and references. Each culture before drug treatment served as its own baseline by showing a unique pattern of discrete tumor fragments distributed within the culture matrix. The disappearance of fluorescent fragments in the drug-treated culture was taken as a positive effect of the drug when compared against control cultures.

What is claimed is:

1. A method for separating viable malignant cell aggregates from a tumor biopsy sample, the method comprising:

separating the tumor biopsy sample into discrete fragments;

suspending the fragments in an aqueous medium such that non-aggregated cells and cellular debris form a supernatant, while aggregates of tumor cells exhibiting a multicellular organization form a sediment; and recovering viable tumor cell aggregates from the sediment.

2. The method of claim 1 wherein the step of separating the sample further includes mechanically cleaving the sample into fragments.

3. The method of claim 1 wherein the step of separating the sample further includes chemically treating the sample with an enzymatic reagent.

4. The method of claim 3 wherein the enzymatic reagent is selected from the group consisting of collaganese, trypsin, chymotrypsin, DNAase, and RNAase.

5. The method of claim 4 wherein the enzymatic reagent is collagenase.

6. The method of claim 1 wherein the step of suspending the fragments in an aqueous medium further includes suspending the fragments in a first, serum-containing medium; decanting the supernatant and first medium; and then resuspending the sediment in a second, serum-free medium.

7. The method of claim 1 wherein the method further comprises contacting the sediment with a fluorogenic substrate whereby aggregates containing viable cells will take up the substrate and exhibit fluorescence, and then recovering the aggregates that exhibit fluorescence.

8. The method of claim 1 wherein the method further comprises recovering tumor cell aggregates that retain the structure and organization of the original tumor, and culturing the recovered tumor cell aggregates to establish a cell culture.

9. A method of separating visible malignant cell aggregates from a tumor biopsy sample, the method comprising:

separating the tumor biopsy sample into discrete fragments;

suspending the fragments in an aqueous medium such that non-aggregated cells and cellular debris form a supernatant, while aggregates of tumor cells exhibiting a multi-cellular organization form a sediment;

contacting the sediment with a fluorogenic substrate whereby aggregates containing viable cells will take up the substrate and exhibit fluorescence; and recovering viable tumor cell aggregates which exhibit fluorescence from the sediment.

10. The method of claim 9 wherein the method of separating further includes mechanically cleaving the sample into fragments.

11. The method of claim 10 wherein the step of cleaving the sample into fragments further comprises cleaving the sample into fragments ranging from about 0.3 cubic millimeters to about 5.0 cubic millimeters in size.

12. The method of claim 10 wherein the mechanically cleaved fragments are further dissociated by shearing.

13. The method of claim 9 wherein the step of separating the sample further includes chemically treating the sample with an enzymatic reagent.

14. The method of claim 13 wherein the enzymatic reagent is chosen from the group of collagenase, trypsin, chymotrypsin, DNAase, and RNAase.

15. The method of claim 14 wherein the enzymatic reagent is collagenase.

16. The method of claim 9 wherein the step of suspending the fragments in an aqueous medium further includes suspending the fragments in an isotonic aqueous medium.

17. The method of claim 6 wherein the isotonic medium is an isotonic tissue culture medium.

18. The method of claim 9 wherein the step of suspending the fragments in an aqueous medium further includes suspending the fragments in a first, serum-containing medium; decanting the supernatant and first medium; and then resuspending the sediment in a second, serum-free medium.

19. A method of assaying the sensitivity of biopsied tumor cells to therapeutic agents, the method comprising:
  separating biopsy sample from a tumor into discrete fragments;
  suspending the fragments in an aqueous medium such that non-aggregated cells and cellular debris form a supernatant, while aggregates of tumor cells exhibiting a multi-cellular organization form a sediment,
  recovering viable tumor cell aggregates that retain the structure and organization of the original tumor from the sediment,
  culturing the recovered aggregates to establish a cell culture;
  exposing the cell culture to a therapeutic agent; and
  measuring changes in the cell culture following exposure to said agent as an indicator of the sensitivity of the cells to the agent.

* * * * *